United States Patent [19]

Ryan

[11] Patent Number: 5,066,286
[45] Date of Patent: Nov. 19, 1991

[54] SAFETY MULTIPLE SAMPLE LUER ADAPTER ASSEMBLY

[75] Inventor: Dana W. Ryan, Franklin, Tenn.

[73] Assignee: Ryan Medical, Inc., Brentwood, Tenn.

[21] Appl. No.: 610,538

[22] Filed: Nov. 8, 1990

Related U.S. Application Data

[63] Continuation-in-part of Ser. No. 520,239, May 7, 1989.

[51] Int. Cl.$^5$ .............................................. A61M 5/00
[52] U.S. Cl. ..................................... 604/240; 128/763
[58] Field of Search ............... 604/240, 241, 242, 187, 604/192, 195; 128/763, 764, 765

[56] References Cited

U.S. PATENT DOCUMENTS

| | | | |
|---|---|---|---|
| 3,884,229 | 5/1975 | Raines et al. | 604/242 |
| 4,398,544 | 8/1983 | Nugent et al. | 128/763 |
| 4,418,703 | 12/1983 | Hoch et al. | 128/763 |
| 4,679,571 | 7/1987 | Frankel et al. | 128/765 |
| 4,740,205 | 4/1988 | Seltzer et al. | 604/241 |
| 4,841,985 | 6/1989 | Wanamaker | 128/763 |
| 4,935,014 | 6/1990 | Haber | 604/240 X |

*Primary Examiner*—John D. Yasko
*Attorney, Agent, or Firm*—David P. Gordon

[57] ABSTRACT

A safety multiple sample luer adapter assembly is provided having a male connector and a rear blood tube holder each of which is provided with cooperative locking and anti-rotational devices. The locking device of the male connector is a ramp which terminates in a shoulder which in turn terminates in a groove, while the locking device of the rear blood tube holder is a ramp terminating in a seat. The anti-rotational device of the male connector comprises protrusions on the middle portion of the male connector, while the anti-rotational device of the rear blood tube holder comprises notches in a front cylindrical portion of the rear blood tube holder. In assembly, the male connector is aligned with its protrusions engaging the notches of the blood tube holder, and the ramp and shoulder of the male connector are forced past the ramp of the rear blood tube holder until the end of the shoulder of the male connector engages the seat of the rear blood tube holder. In this manner the male connector cannot be removed from and cannot rotate in the rear blood tube holder. After use of the safety multiple sample luer adapter assembly, the assembly can be disposed of without danger of needlesticks, as the rear needle is shielded by the rear blood tube holder.

20 Claims, 1 Drawing Sheet

SAFETY MULTIPLE SAMPLE LUER ADAPTER ASSEMBLY

This is a continuation-in-part of Ser. No. 07/520,239 filed on May 7, 1990 which is hereby incorporated by reference herein in its entirety.

BACKGROUND OF THE INVENTION

This invention relates to medical devices for drawing blood samples, and more particularly to a safety multiple sample luer adapter assembly that makes it easier to draw blood samples from patients, and at the same time, provides substantial protection against needlesticks and blood borne contaminates.

Drawing blood samples from patients is often a difficult task especially if a patient has small and/or difficult veins as is frequently the case with children, small women or the elderly. It is not unusual for a patient with small veins to be stuck more than once using standard blood collection needles before the needle is positioned properly in the vein to draw the blood sample. This problem can cause the patient physical distress and considerable anxiety. Under such conditions, the medical staff is also subjected to increased stress because of the patient's reaction to the difficulty of the procedure.

Winged needle devices, which give the phlebotomist greater control of the venipuncture procedure, can be helpful in solving the problem of taking blood samples from patients with small veins. The smaller winged needle device, because of its reduced size, allows the medical staff to position the needle more accurately, which significantly reduces the number of times a patient must be stuck with the needle to produce satisfactory blood sampling. However, standard winged needle devices do not have means for accepting blood collection vacuum tubes which provide negative pressure for drawing blood and in which the drawn blood is collected.

In order to permit the use of a winged needle device with a blood collection vacuum tube, it was proposed in U.S. Pat. No. 4,140,108 issued to Nugent to provide a blood collection assembly with a rear needle adapter for use in taking blood samples. The blood collection assembly of Nugent is comprised of several parts, including a rear needle adapter, and flexible tubing with hubs and needles on each end (one venipuncture needle and one rear needle for puncturing a stopper on a vacuum tube). The venipuncture needle is in open communication with the tubing and is held in the tubing by attachment to the hub. The rear needle is attached to the flexible tubing via the rear hub. The rear hub has external male helical threads which permit it to be screwed to and unscrewed from the forward hub portion of a standard rear blood tube holder which has reciprocating internal female helical threads. The standard rear blood tube holder also includes a receiving cylinder which is open at one end for receiving blood collection vacuum tubes.

In using the device disclosed by the Nugent patent, the rear needle attached to the male threaded hub is placed in the forward hub portion of a standard rear blood tube holder, and the rear hub on the flexible tubing is mated with the forward hub portion of a standard rear blood tube holder by screwing the two together. The assembly is then ready to have standard blood collection vacuum tube(s) inserted in the receiving cylinder of the rear blood tube holder, such that the rear needle will puncture the stopper of the blood collection vacuum tube and blood will be collected. When the blood sampling procedure is finished, the venipuncture needle is removed from the patient's vein, and the rear needle is removed from the standard rear blood tube holder by unscrewing the hub holding the rear needle. The rear blood tube holder is then saved for subsequent uses. However, upon disassembly, the venipuncture and rear needles are contaminated and left completely exposed increasing the possibility of unwanted needlesticks occurring.

SUMMARY OF INVENTION

It is therefore the primary object of the invention to provide a safety multiple sample luer adapter blood collection assembly which can be used with standard or safety winged needle venipuncture devices and which shields a rear needle which is permanently locked inside a rear blood tube holder, thereby significantly reducing the possibility of needlesticks and/or blood borne contaminates.

According to a first aspect of the invention, the safety luer adapter assembly of the invention preferably comprises a male connector and a hollow rear blood tube holder. The male connector has hollow first and second ends and a hollow needle, the hollow first and second ends defining a throughbore that is connected with the needle. The first end of the male connector holds the needle and includes a first locking means for locking with reciprocal means of the hollow rear blood tube holder. The second end of the male connector has a coupling such as a luer lock for coupling to a standard female luer lock adapter which is typically connected to a winged needle device. The hollow rear blood tube holder has an outer wall which forms a receiving cylinder with an open rear end for receiving blood collection vacuum tubes, and a front end having an opening for accepting the hollow front end of the male connector, the front end having locking means that mates to the male adapter.

The locking configuration on the male connector uses a ramp portion of increasing diameter and an increased diameter shoulder, while the locking configuration on the rear tube holder uses a ramp of decreasing diameter which terminates in an increased diameter seat. The ramp and shoulder of the male connector are slid past the ramp at the front end of the rear blood tube holder such that the shoulder passes the ramp, rests in the seat, and cannot be removed from the rear blood tube holder because of the back face of the rear blood tube holder ramp. To expedite the movement of the increased diameter shoulder past the decreasing diameter ramp, the shoulder may be notched. To prevent rotation of the male connector and the rear blood tube holder, at least portions of the outer surface of the first end of the male connector and corresponding portions (in the mated position) of the inner surface of the front end of the rear blood tube holder are reciprocally notched.

Additional objects and advantages of the invention will become apparent to those skilled in the art upon reference to the detailed description in conjunction with the accompanying drawings.

BRIEF DESCRIPTION OF THE DRAWINGS

FIG. 1b is a cross section along axis A—A through the male connector of FIG. 1a;

FIG. 1c is an enlarged front view of the male connector of FIG. 1a;

DETAILED DESCRIPTION OF THE INVENTION

Figure 1A:
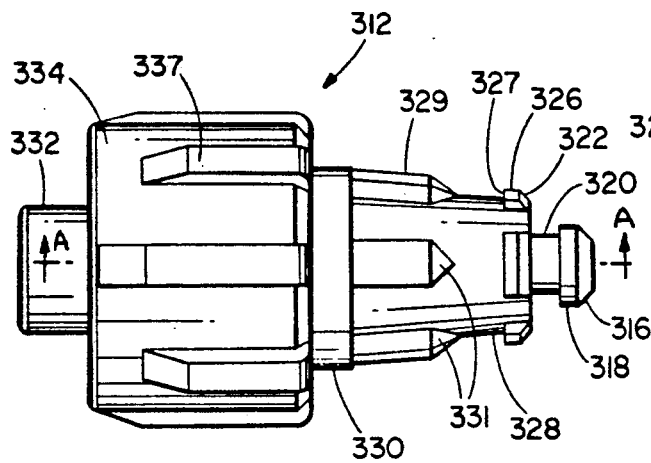
FIG. 1a is an enlarged perspective of the male connector of the invention.
Figure 1C:
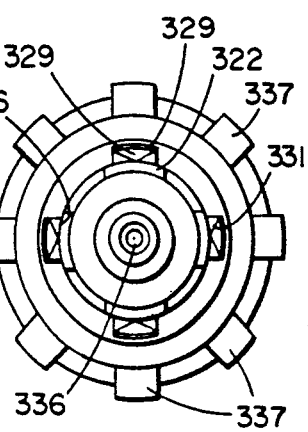
Figure 1B:
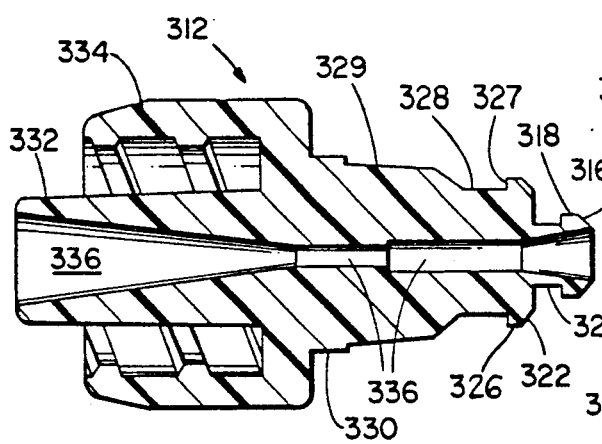
Figure 2B:
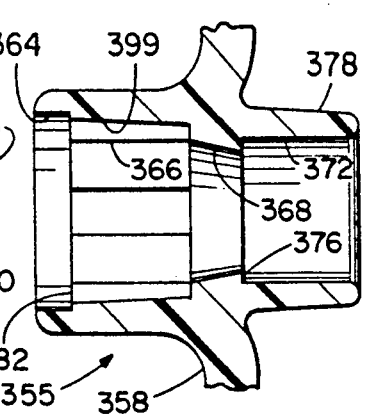
FIG. 2b is an enlarged view of the cross section through the front end of the rear blood tube holder of FIG. 1.
Figure 2A:
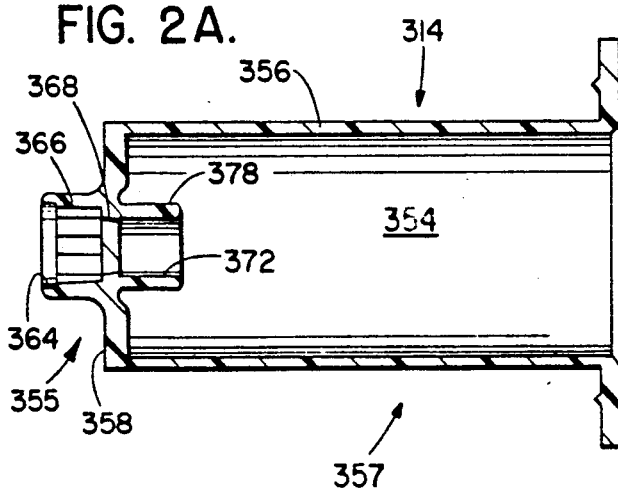
FIG. 2a is a cross section through the rear blood tube holder of the invention.
Figure 2C:
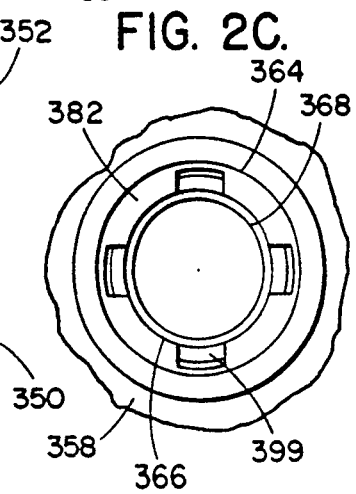
FIG. 2c is a partial front end view of the rear blood tube holder of FIG. 2b.

The safety multiple sample luer adapter assembly 300 of the invention comprises a male connector 312 shown in FIGS. 1a-1c and a rear blood tube holder 314 shown in FIGS. 2a-2c. The male connector 312 as shown in FIGS. 1a-1c has a hollow front end with a nose 318 having a bevel 316 on the end of the nose, a groove 320 of reduced outer diameter relative to the outer diameter of the nose 318 (the nose and groove for purposes described in the parent application hereto), a segmented ramp 322 which is of greater diameter than the diameter of the nose 318, which increases in diameter as it extends away from the nose, and which terminates in a segmented locking shoulder 326 of relatively constant diameter. The segmented locking shoulder 326 in turn terminates with a rear abutment surface 327. Rearward of the front end of the male connector 312 is a hollow middle portion which starts with a groove 328 of diameter smaller than segmented locking shoulder 326, continues with preferably ramped anti-rotational protrusions or ribs 329, and terminates with stop collar 330. The anti-rotational protrusions 329 preferably start in an arrow configuration 331 (best seen in FIG. 1a and 1c) for self-centering purposes, and the protrusions 329 preferably increase in diameter as they extend from groove 328 toward the stop collar 330.

Rearward of the hollow middle portion of the male connector is a rear end which comprises a standard male luer lock. The male luer lock has a male luer section 332 with an outer surface which tapers according to standard male luer specifications, and a threaded locking section 334 according to luer lock specifications. The threaded locking section 334 preferably includes outwardly extending ribs 337 which permits a user of the assembly to more easily grip the assembly while mating the assembly with a female luer lock mechanism.

As aforestated, the front end, middle portion, and rear end of the male connector 312 are hollow, and they together provide a continuous throughbore 336 of varying size. The portion of tapered bore 336 that begins at the nose 318 is arranged to permit a hollow needle (not shown) to be permanently attached therein, such as by gluing or bonding. Of course, the needle may be permanently attached via injection molding of the assembly.

Turning to FIGS. 2a-2c, the rear blood tube holder 314 is seen to have a front mating portion 355 and rear receiving cylindrical portion 357. The receiving cylindrical portion 357 has a circular opening 350 surrounded by a flange 352, and a chamber 354 formed by receiving cylinder wall 356. Receiving cylinder portion 357 terminates with a front end wall 358 which supports and is closed around front mating portion 355 which extends outward from the front wall 358. The front end of the front mating portion begins with a hollow cylinder 364 which has an inside diameter substantially equal to the diameter of the male connector stop collar 330 shown in FIGS. 1a and 1b, and with a depth substantially equal to the length of the stop collar. Adjacent to hollow cylinder 364 is a grooved reduced diameter cylinder 366 with an inside diameter substantially equal to the outside diameter of the male connector segmented shoulder 326. As indicated in FIGS. 2b and 2c, grooves or notches 399 are formed in reduced diameter cylinder 366. The grooves 399 increase the inner diameter of the reduced diameter cylinder 366 at certain locations and are sized to receive the anti-rotational protrusions 329 of the male connector; i.e. the inner diameter of grooves 399 is substantially equal to the outer diameter of protrusions 329 and is preferably appropriately tapered.

The notched reduced diameter cylinder 366 of the rear blood tube holder terminates in a ramp 368. Ramp 368 decreases in diameter as it extends toward chamber 354 and terminates in a seat 376 which is also defined by the interior cylindrical wall 372 of collar 378. The collar 378 protrudes into the hollow middle portion (chamber) 354 of the rear blood tube holder 314. The horizontal distance between seat 376 and the notched seat 382 formed by hollow cylinder 364 and notched hollow cylinder 366 of the rear blood tube holder is substantially the same as the horizontal distance between the termination of the male connector ratcheted shoulder 27 and the beginning of stop collar 330 shown in FIGS. 1a and 1b. Also, the horizontal length of stop collar 30 is preferably approximately equal to the horizontal length of hollow cylinder 364.

In connecting the male connector to the rear blood tube holder to make up the invention assembly 300 shown as FIGS. 1a and 2a, the male connector nose 318 is inserted in the rear blood tube holder front mating portion hollow cylinder 364. The nose 318 of the male connector is slid past the hollow cylinder 364 and into the reduced diameter cylinder 366 and then past ramp 68. At approximately that time, or some time before, the male connector 312 and the rear blood tube holder 314 are rotationally aligned such that the protrusions 329 on the middle portion of the male connector will properly slide into the grooves 399 in the reduced hollow cylinder 364 of the blood tube holder 314. Rotational alignment is expedited by the arrow configuration 331 of the front end of the anti-rotational protrusions 329. In fact, depending on the circumferential size of the protrusions 399 relative to the entire circumference, rotational alignment may be automatic, as at least one protrusion 329 may always partly engage a groove 399 and cause rotation of the male connector relative to the rear blood tube holder during assembly. With the male connector and blood tube holder aligned (or during alignment), the segmented ramp 322 and shoulder 326 of the male connector is slid along rear blood tube holder ramp 368 while protrusions 329 slide in grooves 399. Because the ramp 322 and shoulder 326 of the male connector are segmented, they deform to the contour of the rear blood tube holder ramp 368 as they slide therethrough. As the segmented shoulder 326 clears seat 376 of the rear blood tube holder, the deformed segmented ramp 322 and shoulder 326 return substantially to their original shape. If an attempt is made to pull the male connector out of the rear blood tube holder, the ratcheted shoulder 326 is restrained from being pulled out by rear tube holder seat 376 bearing on abutment surface 327. Since the male connector protrusions 329 are sitting in the rear blood tube holder grooves 399, no rotation of the male connector relative to the rear tube holder is possible. In this manner the male connector is permanently installed in the rear blood tube holder.

In use, the male connector is attached to the rear blood tube holder as described. The assembly is then used as described in the parent application hereto Ser. No. 07/520,239, except that a female luer lock is used to connect to the male luer lock (332 and 334) of the male connector 312. If a small sample of blood is required as is the case n some pediatric and other situations, then a special reduced diameter blood collection vacuum tube adapter discussed in Ser. No. 07/520,239 is used.

There has been described and illustrated herein a safety multiple sample luer adapter assembly. While a particular embodiment of the invention has been described, it is not intended that the invention be limited thereby, as it is intended that the invention be as broad in scope as the art will allow. Thus, it will be understood by those skilled in the art that while the locking shoulder and ramp of the male connector were described as segmented for purposes of deformation, depending on the tolerances and materials used, the locking shoulder and ramp could be continuous. Also, while self-aligning protrusions were described for aligning the protrusions of the male connector in the notches of the rear blood tube holder, it will be appreciated that alignment could be obtained by other means. Therefore, it will be appreciated by those skilled in the art that yet other modifications could be made to the provided invention without deviating from its spirit and scope as so claimed.

I claim:

1. A safety luer adapter assembly for coupling a fluid conduit means to a fluid collection means, said safety luer adapter assembly comprising:
   a) a male connector having hollow first and second end portions, said hollow first and second end portions defining a throughbore in fluid communication with said fluid conduit means, said first end portion having first locking means, said male connector having first anti-rotational means, and said second end portion having coupling means for coupling to the fluid conduit means; and
   b) a hollow rear blood tube holder with an outer wall defining a receiving cylinder with an open rear end for receiving the fluid collection means, and a front end having an opening therein for accepting at least a portion of said hollow first end portion of said male connector, said front end of said hollow rear blood tube holder having second locking means, and said hollow rear blood tube holder having second anti-rotational means,
   wherein in assembling said safety luer adapter assembly said first and second locking means are brought into permanent locking engagement, and said first and second anti-rotational means are brought into engagement to prevent rotation of said male connector relative to said hollow rear blood tube holder.

2. A safety luer adapter assembly according to claim 1, wherein:
   said first locking means is on the outer surface of said first end portion of said male connector, and said second locking means is on the inner surface of said front end of said hollow rear blood tube holder.

3. A safety luer adapter assembly according to claim 2, wherein:
   said outer surface of said first end portion of said male connector comprises a first ramp of increasing diameter as it extends from said first end portion toward said second end portion, and a shoulder of relatively constant outer diameter, said first ramp terminating in a first end of said shoulder, said shoulder having a second end terminating in portion of reduced diameter relative thereto, and
   said inner surface of said front end of said hollow rear blood tube holder comprises a second ramp of decreasing inner diameter as it extends from said front end to said open rear end, said second ramp terminating in a chamber of inner diameter at least as large as said outer diameter of said shoulder, and said shoulder being of larger outer diameter than the inner diameter of said second ramp termination such that said termination of said second ramp and said shoulder form abutting locking surfaces.

4. A safety luer adapter assembly according to claim 3, wherein:
   said first ramp is a first segmented ramp, and said shoulder is a segmented shoulder.

5. A safety luer adapter assembly according to claim 1, wherein:
   said male connector further includes a hollow middle portion between said hollow first and second end portions, said hollow middle portion having at least one outwardly extending protrusion which constitutes said anti-rotational means, and
   at least a portion of said front end of said hollow rear blood tube holder comprises a notched member with at least one notch arranged to receive and hold said at least one outwardly extending protrusion when said male connector and said hollow rear blood tube holder are in permanent locking engagement.

6. A safety luer adapter assembly according to claim 5, wherein:
   said at least one outwardly extending protrusion comprises a plurality of outwardly extending protrusions, and said at least one notch comprises a plurality of notches.

7. A safety luer adapter assembly according to claim 6, wherein:
   said outwardly extending protrusions taper in two directions to form self-aligning protrusions.

8. A safety luer adapter assembly according to claim 3, wherein:
   said male connector further includes a hollow middle portion between said hollow first and second end portions, said hollow middle portion having at least one outwardly extending protrusion which constitutes said anti-rotational means, and
   at least a portion of said front end of said hollow rear blood tube holder comprises a notched member arranged to receive and hold said at least one outwardly extending protrusion when said male connector and said hollow rear blood tube holder are in permanent locking engagement.

9. A safety luer adapter assembly according to claim 8, wherein:
   said at least one outwardly extending protrusion comprises a plurality of outwardly extending protrusions, and said at least one notch comprises a plurality of notches.

10. A safety luer adapter assembly according to claim 9, wherein:

said outwardly extending protrusions taper in two directions to form self-aligning protrusions.

11. A safety luer adapter assembly according to claim 1, wherein said hollow first end portion of said male connector includes a nose portion and a groove forward of said first ramp, said groove being between said nose portion and said first ramp and of an outer diameter smaller than said nose portion, and said nose portion being of outer diameter smaller than said outer diameter of said ramp.

12. A safety luer adapter assembly according to claim 4, wherein:

said hollow first end portion of said male connector includes a nose portion and a groove forward of said first segmented ramp, said groove being between said nose portion and said first segmented ramp and of an outer diameter smaller than said nose portion, and said nose portion being of outer diameter smaller than said outer diameter of said segmented ramp.

13. A safety luer adapter assembly according to claim 1, wherein:

said coupling means of said second portion of said male connector comprises a male luer lock having a male luer portion and a threaded locking portion.

14. A safety luer adapter assembly according to claim 13, wherein:

said threaded locking portion of said male luer lock has an outer surface, and said outer surface has a gripping means.

15. A safety luer adapter assembly according to claim 14, wherein:

said gripping means comprises a plurality of ribs extending axially parallel to a long axis of said male connector.

16. A safety luer adapter assembly according to claim 5, wherein:

said coupling means of said second portion of said male connector comprises a male luer lock having a male luer portion and a threaded locking portion.

17. A safety luer adapter assembly according to claim 16, wherein:

said threaded locking portion of said male luer lock has an outer surface, and said outer surface has a gripping means.

18. A safety luer adapter assembly according to claim 17, wherein:

said gripping means comprises a plurality of ribs extending axially parallel to a long axis of said male connector.

19. A safety luer adapter assembly according to claim 10, wherein:

said coupling means of said second portion of said male connector comprises a male luer lock having a male luer portion and a threaded locking portion.

20. A safety luer adapter assembly according to claim 19, wherein:

said threaded locking portion of said male luer lock has an outer surface, and said outer surface has a gripping means, said gripping means comprises a plurality of ribs extending axially parallel to a long axis of said male connector.

* * * * *